(12) United States Patent
Weaver

(10) Patent No.: US 6,187,565 B1
(45) Date of Patent: Feb. 13, 2001

(54) PHOTOCONVERSION OF ORGANIC MATERIALS INTO SINGLE-CELL PROTEIN

(76) Inventor: Paul F. Weaver, 13130 W. 66th Pl., Golden, CO (US) 80401

( * ) Notice: Under 35 U.S.C. 154(b), the term of this patent shall be extended for 0 days.

(21) Appl. No.: 07/959,519

(22) Filed: Oct. 13, 1992

Related U.S. Application Data

(63) Continuation of application No. 07/739,368, filed on Aug. 2, 1991, now abandoned.

(51) Int. Cl.[7] .............................. C12N 1/20; C12N 1/12
(52) U.S. Cl. ................. 435/71.1; 435/252.1; 435/253; 435/804
(58) Field of Search ............................. 435/71.1, 252.1, 435/804, 253

(56) References Cited

U.S. PATENT DOCUMENTS

| | | |
|---|---|---|
| 3,525,671 | 8/1970 | Hitzman . |
| 3,649,459 | 3/1972 | Wolnak et al. . |
| 4,115,593 | 9/1978 | Henry . |
| 4,306,026 * | 12/1981 | Maslen et al. . |
| 4,359,530 | 11/1982 | Brown . |
| 4,429,043 | 1/1984 | Paton . |
| 4,439,523 * | 3/1984 | Malick et al. . |
| 4,467,035 | 8/1984 | Harasawa et al. . |
| 4,596,778 | 6/1986 | Hitzman . |
| 4,859,588 * | 8/1989 | Sublette . |
| 4,919,813 * | 4/1990 | Weaver . |

OTHER PUBLICATIONS

Vandermark et al. *The Microbes.* 1987. pp. 133 & 263.*
Vrati. *Applied Microbiology and Biotechnology.* 1984 p. 199–202.*

* cited by examiner

*Primary Examiner*—Leon B. Lankford, Jr.

(57) ABSTRACT

A process is described for converting organic materials (such as biomass wastes) into sterile, high-grade bacterial protein suitable for use an animal feed or human food supplements. In a preferred embodiment the process involves thermally gasifying the organic material into primarily carbon monoxide, hydrogen and nitrogen products, followed by photosynthetic bacterial assimilation of the gases into cell material, which can be as high as 65% protein. The process is ideally suited for waste recycling and for food production under zero-gravity or extra-terrestrial conditions.

19 Claims, 3 Drawing Sheets

BUBBLE TOWER DESIGN

PHOTOCONVERSION OF ORGANIC MATERIALS INTO SINGLE-CELL PROTEIN

This is a Continuation of application Ser. No. 07/739,368 filed Aug. 2, 1991 now abandoned.

The United States Government has rights in this invention under Contract No. DE-AC02-83CH10093 between the United States Department of Energy and the Solar Energy Research Institute, a Division of the Midwest Research Institute.

BACKGROUND OF THE INVENTION

1. Field of the Invention

The present invention relates generally to conversion of organic materials into protein. Specifically, the present invention relates to a process for converting biomass wastes, for example, into high-grade bacterial protein suitable for use as animal feed or human food supplements.

2. Description of the Prior Art

Harmless microorganisms have long been used by man for the production of beer, wine, cheeses, breads, sausages, yogurts, soy sauce, and other foodstuffs. During both World Wars, Germany pioneered work on growing microbes on relatively inexpensive substrates, such as molasses, not to alter the taste of foods, but rather to produce edible microbial cell mass for use as a meat substitute or meat extender. Protein produced from single-celled microorganisms for use as animal feed or human food has since become known as single-cell protein (SCP).

Free-world production of SCP today is about $2 \times 10^6$ tons per year which is used for food or food supplements. SCP is in economic competition with relatively expensive soybean meal, fish meal, egg, or skim milk proteins for common uses. Pruteen, a commercial production of Imperial Chemical Industries in Great Britain, is a SCP made by non-$N_2$-fixing bacteria growing on methanol derived from fossil fuels, as is the case with most other SCP products. The current market price for Pruteen is about 50 cents per pound with about three-fourths of the operating expenses attributable to the costs for methanol, ammonia, and oxygen.

Use of inexpensive biomass waste materials for SCP production would greatly benefit the economics of the process. However, no microbe known will directly convert more than a small fraction of lignocellulosic waste substrates into SCP over a reasonably short period of time. In general, aerobic bacteria convert about 25% of easily digestable substrates into new cell mass, and anaerobic bacteria convert only about 7%. Furthermore, much of the lignocellulosic materials are not easily digested and may take months to be catabolized, if at all.

Each of the five billion people on earth ideally needs about 2600 calories of food per day to maintain health, which is equivalent to about 20 quads of foodstuff energy per year worldwide (about one quad of food energy is ingested per year by the total U.S. population). Approximately 20%, or $12 \times 10^6$ metric tons, of the U.S. citizen's caloric intake is in the form of protein obtained from animal or vegetable sources. The national requirement for protein is actually considerably larger, since it takes about 10 pounds of feed to make a pound of beefsteak or 3 pounds of feed to make a pound of chicken. It has been estimated that even if all of the available protein worldwide in 1980 had been equitably distributed, there still would have been a shortfall of $10^7$ metric tons (I. Goldberg, 1985, *Single Cell Protein*, Springer-Verlag, New York). The protein shortage will increase 2.5-fold by the year 2000.

Direct and indirect fuel consumption represent a major cost in the production of food. About one-third of the fossil fuel used in agricultural production and its transportation is used by the Haber process for the synthesis of ammonia-based fertilizer. A few leguminous crops (e.g., peas, peanuts, and soy beans) employ a symbiosis with $N_2$-fixing bacteria in their roots to partially fulfill their requirement for ammonia. Even so, lack of sufficient ammonia is rate-limiting for growth, and application of additional nitrogenous fertilizer will enhance productivity. Also, growing plant crops to raise food requires long growing seasons.

A method to rapidly produce an inexpensive, high-quality protein product without ammonia fertilization would have immense value and potential primarily for use in producing animal feed, but also, under certain conditions, in producing human food. The capacity for high-rate production would ameliorate the effects of drought, famine, or national disasters. It should also decrease the demands for land and energy currently allocated for growing animal-feed crops. Existing schemes for single-cell protein synthesis involve use of expensive or potentially toxic petroleum-based organic substrates and nitrogenous fertilizers.

There has not heretofore been provided a technique or process for simple and effective conversion or organic materials into protein suitable for use as animal feed or human food supplements.

SUMMARY OF THE INVENTION

It is an object of this invention to provide a process for the conversion of organic wastes to hydrogen and carbon monoxide and then, with nitrogen-containing substances present, conversion to single-cell protein using photosynthetic bacteria.

It is another object of this invention to utilize photosynthetic bacteria in a process for producing single-cell protein in an effective and efficient manner.

It is another object of this invention to utilize photosynthetic bacteria and solar energy for producing single-cell protein which is suitable for use as an animal feed or human food supplement.

It is another object of this invention to provide a process for converting low-grade organic waste into bacteria cell mass which is high in protein.

It is yet another object of this invention to provide a process for converting carbon monoxide, hydrogen, and nitrogen into single-cell protein in an efficient manner.

Additional objects, advantages, and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

To achieve the foregoing and other objects and in accordance with the purpose of the present invention, as embodied and broadly described herein, the invention may comprise a process for producing single-cell protein, wherein the process includes the steps of:

(a) combusting organic material in limited oxygen or air to produce gaseous nutrients comprising carbon monoxide, hydrogen and nitrogen;

(b) feeding the gaseous nutrients to photosynthetic bacteria; and (c) exposing the bacteria to radiant energy, whereby the gaseous nutrients are assimilated into bacterial cell mass which is high in protein.

The process of this invention is useful for rapidly converting low-grade biomass wastes, such as lignocellulosics, into sterile, high-grade bacterial protein suitable for use as animal feed or human food supplements. The waste materials are thermally gasified in limited oxygen or air to form primarily carbon monoxide, hydrogen, and nitrogen products, followed by photosynthetic bacterial assimilation of the gases into cell material, which can be as high as 65% protein. The overall process is nearly quantitative, driven by the energy of sunlight, for example. Photosynthetic bacteria are highly productive, with mass-doubling times as low as 90 minutes, and offer potential as a one-or two-day protein crop.

In addition to terrestrial use, the process of the invention is ideally suited for waste recycling and food production under zero-gravity or extraterrestrial conditions.

The nutrients (carbon monoxide, hydrogen, and nitrogen) provided by combusting low-grade waste materials in limited oxygen or air, are recombined by photosynthetic bacteria into a high-protein single-cell product. The process can be carried out under anaerobic conditions, but this is not required.

Other advantages of the process of the invention will be apparent from the following detailed description.

BRIEF DESCRIPTION OF THE DRAWINGS

The accompanying drawings, which are incorporated into and form a part of the specification, illustrate preferred embodiments of the present invention, and together with the description, serve to explain the principles of the invention.

DETAILED DESCRIPTION OF THE PREFERRED EMBODIMENTS

Figure 1:
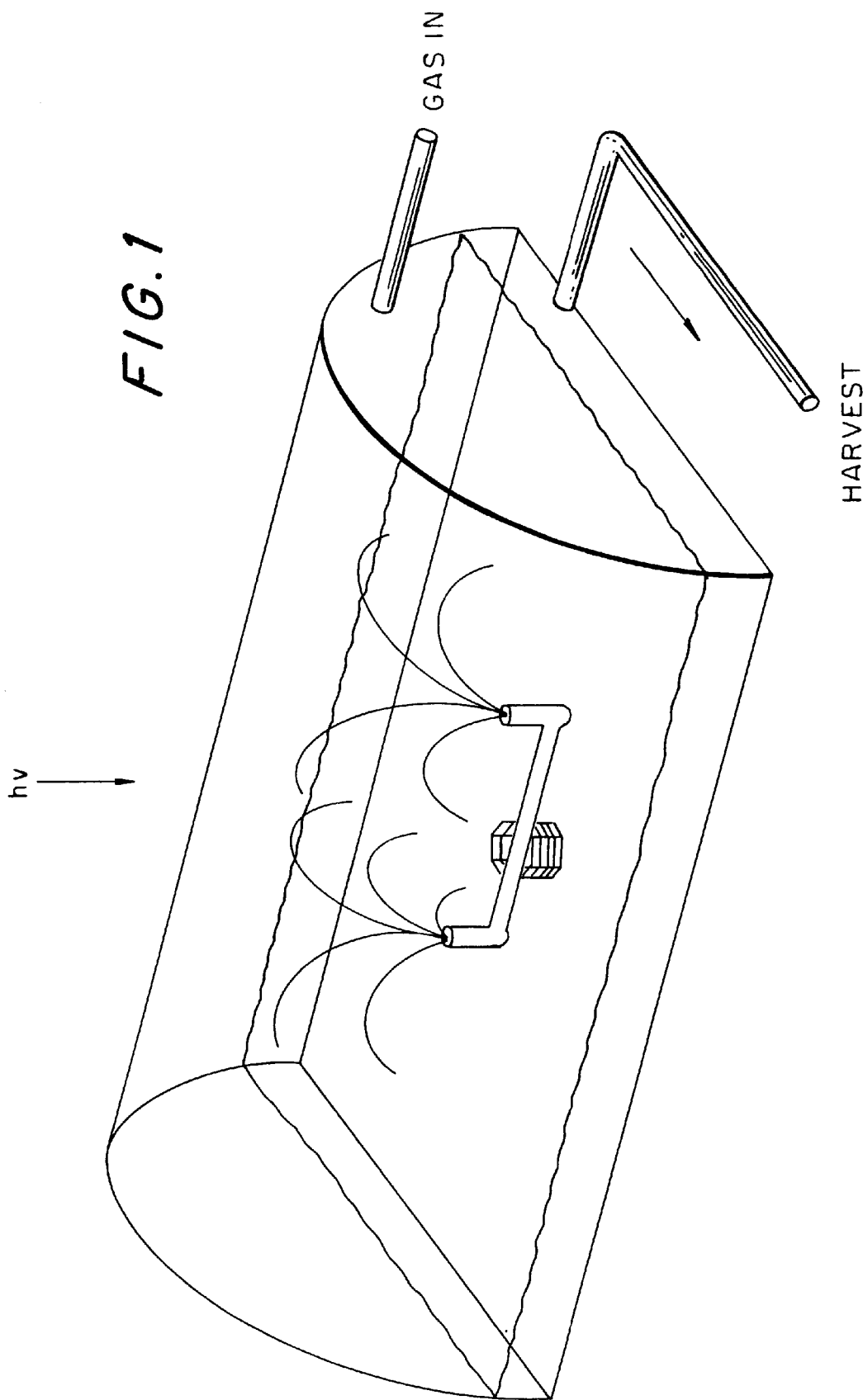
FIG. 1 illustrates one embodiment of reactor which is useful in this invention.

The organic materials which may be converted into single-cell protein in accordance with the principles of this invention are carbonaceous materials which are or can be gasified including, for example, natural gas, coal, petroleum fractions, shale oil, peat, municipal solid waste, agricultural waste, forestry residues, organic chemical waste, manures, or other forms of biomass. Steam-reformed natural gas also generates similar gaseous products.

The present invention provides techniques for converting the gaseous nutrients into single-cell protein in a rapid and efficient manner.

Thus, the techniques of the present invention pertain to the conversion of synthesis gas (i.e., hydrogen and carbon monoxide from oxygen-blown gasifiers or steam-reformed natural gas) or producer gas (i.e., hydrogen, carbon monoxide and nitrogen from air-blown gasifiers) into single-cell protein, regardless of where the gaseous nutrients come from.

Of course, in order to produce single-cell protein there must be a source of nitrogen present. The nitrogen may be from air used to fire the gasifier when producing the gaseous nutrients from organic materials, it may be added as pure nitrogen gas, or it may be added as ammonia, urea, nitrates, or other combined forms of nitrogen.

The bacteria capable of using syngas or producer gas for growth are all members of the bacterial order Rhodospirilales of photosynthetic or phototropic bacteria. Not all members of this order are useful in this invention however. The photosynthetic bacteria which are useful in this invention are capable of growing on carbon monoxide.

More than 300 strains of photosynthetic bacteria have been isolated from natural soil and water samples through enrichment cultures growing on carbon monoxide as the sole source of carbon. No particular species of photosynthetic bacteria dominated the isolates. This capacity for growth on carbon monoxide identifies the unique strains of photosynthetic bacteria which are useful in the practice of this invention.

Useful strains of photosynthetic bacteria have been characterized within the following genera and species, for example, *Rhodocyclus gelatinosus, Rhodopseudomonas palustris, Rhodospirillum molischianum,* and *Rhodopseudomonas capsulata.*

Thermally gasifying organic wastes rapidly converts nearly all of the material into a fairly homogeneous gas, consisting primarily of CO and $H_2$.

$$(CH_2O)_n \xrightarrow{\text{limiting } O_2} n\,CO + n\,H_2$$

If limiting air or enriched $O_2+N_2$ is used for the gasification, the $N_2$ exits in the gas stream unchanged.

$$(CH_2O)_n \xrightarrow{\text{limiting } O_2 + m\,N_2} n\,CO + n\,H_2 + m\,N_2$$

Both CO and $H_2$ can be readily metabolized by a few bacteria, notably strains of photosynthetic bacteria. Nearly all photosynthetic bacterial strains are also able to reduce $N_2$ to the level of ammonia for use in protein synthesis. A few strains of photosynthetic bacteria are able to assimilate CO and $H_2$ while simultaneously reducing $N_2$. These bacteria are able to grow completely autotrophically on $H_2$, CO, and $N_2$. The process is driven by the energy of light.

$$n\,CO + n\,H_2 + m\,N_2 \xrightarrow{h\nu} (CH_2ON_{2m})_n$$

The resultant biomass product is up to 65% protein with all vitamins present. The protein is a complete protein, high in lysine, methionine, and other essential amino acids necessary for animal subsistence. Experiments indicate that the CO and $H_2$ are totally consumed by the photosynthetic bacteria leaving no waste gases for disposal. Therefore, the overall reaction may be shown as:

$$(CH_2O)_n + m\,N_2 \xrightarrow{h\nu} (CH_2ON_{2m})_n$$

In the process described, low-grade combustible wastes such as lignocellulosics can be gasified and rapidly recycled into a high-grade protein crop. The productivity of photosynthetic bacterial SCP can reach as high as 500 g per $m^2$ per day with complex growth media (doubling in cell mass every 90 minutes), which compares extremely favorably with wheat, for example, which generates only about 36 g protein per $m^2$ for an entire summer crops' harvest.

The bacteria is present in an aqueous medium. The pH of the aqueous medium is generally in the range of about 6–10. There are several reasons why it is believed not to be necessary to operate the process under sterile conditions. Carbon monoxide is toxic to most living things, including most potential pathogens. Besides photosynthetic bacteria, probably no other microbe can sustain itself anaerobically with CO as the sole source of both carbon and energy. Lastly, no pathogens are known that can use $N_2$ as the source of cellular nitrogen. If necessary, however, the process can be easily adapted to sterile conditions since the gasification step sterilizes the gaseous substrates.

Unlike methanol- or paraffin-derived SCP there is no problem with toxic substrate residues remaining in the product since the substrates are all gaseous. Conversion of gasified biomass into new cell mass approaches 100% with no waste products.

Figure 2:
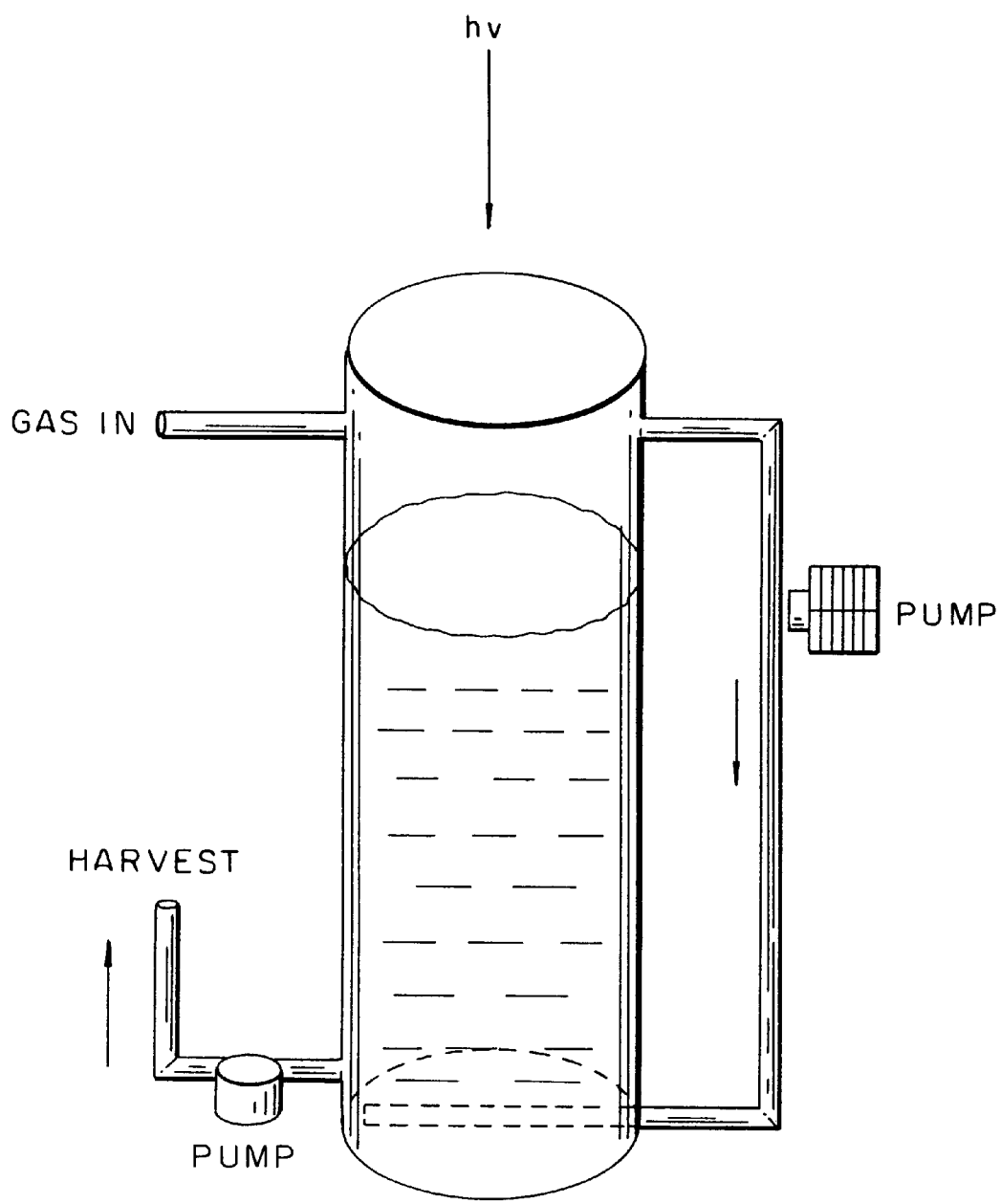
FIG. 2 illustrates another embodiment of a reactor which is useful in this invention.

FIGS. 1 and 2 illustrate two types of useful reactors which may be used in practicing the techniques of this invention. FIG. 1 illustrates a reactor in which an aqueous medium containing the photosynthetic bacteria is forced through sprinklers in a manner such that the liquid medium is sprayed into the gaseous atmosphere of the gaseous nutrients. Other trace mineral nutrients (1) can be leached from the gasifier ash by the bacteria in the aqueous medium, or (2) can be added separately to the aqueous medium. The reactor is transparent to solar energy. The harvest crop of single-cell protein is withdrawn from one end of the reactor.

FIG. 2 illustrates a reactor in which the gaseous nutrients are bubbled upwardly through the liquid medium containing the photosynthetic bacteria. The harvest crop of single-cell protein is withdrawn from the lower end of the reactor, for example.

Another alternative is to place the bacteria on a permeable support which floats on the surface of a liquid medium. In this arrangement the bacteria has maximal exposure to the gasified biomass atmosphere and to solar energy from above, while receiving water and mineral nutrients from the liquid medium.

Figure 3:
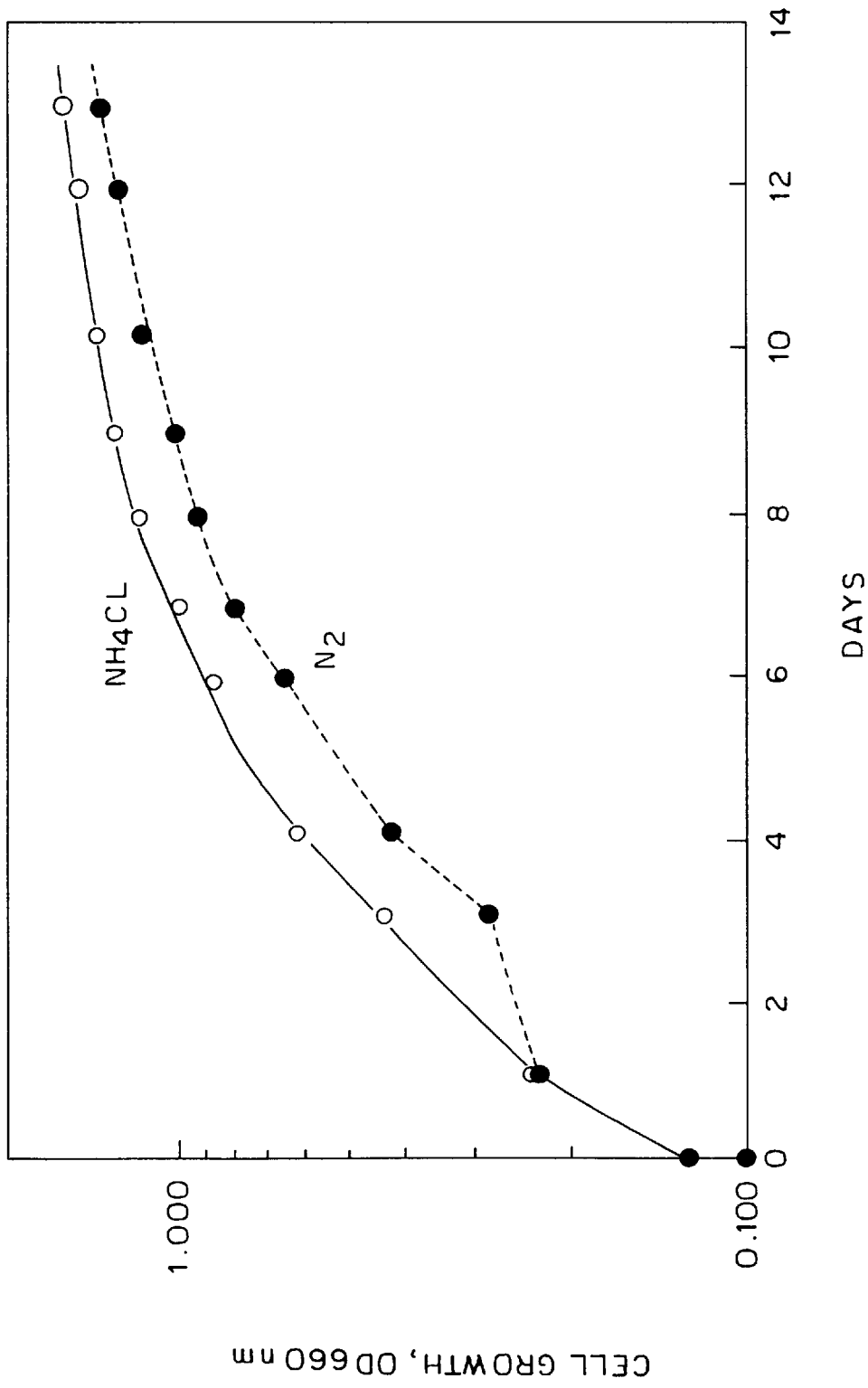
FIG. 3 is a graph illustrating the time course and extent of conversion of gasified biomass into single-cell protein.

FIG. 3 shows the growth of Rhodopseudomonas sp. strain CBS on carbon monoxide and hydrogen (50/50 vol. percent) with time. Cell growth is measured as a function of optical density (OD). Cell mass yields indicate approximately 100% conversion of hydrogen and carbon monoxide into a product having a chemical composition of $C_5H_8O_2N$.

Astronauts on extended space missions are uniquely isolated. At great expense, all food must currently be taken up to earth orbit from the planetary surface and waste materials must be brought down. The process of the present invention is designed to establish a short, solar-driven, food production/waste consumption cycle that is ideally suited for operation in zero-gravity environments or in extraterrestrial colonies, such as the recently proposed moonbase. Ideally, waste recycling and food production would be simplified and expedited to the point where preferred animal products, such as fish or chicken, could be generated in situ. Current systems for waste recycle are slow, incomplete, and produce no directly usable product. Current food production schemes are protein deficient, technologically complex, often slow, and are open-cycled (requiring an earth-based source of fertilizer, oxygen, or organic substrate). NASA, through the CELSS Program, is actively supporting research on fermenter designs for waste recycling and food production under conditions of micro-gravity and scarce resources. Some of the NASA supported work focuses on the production of microalgae for food.

In comparison, photosynthetic bacteria may offer certain advantages in that they grow much more rapidly, are self-fertilizing, and are able to withstand the highly photo-oxidizing conditions of bright sunlight. Other current projects for SCP production that NASA supports involve non-photosynthetic microbial oxidations of sugar, ethanol, or methanol by $O_2$, all of which must be supplied from terrestrial sources. At least one-half, usually three-fourths, of each substrate is oxidized to $CO_2$ during these processes. Fermenter design is greatly complicated by the fact that the $CO_2$ waste product has to be separated from the liquid medium and substrate $O_2$, which is difficult to accomplish at zero gravity. The process of the present invention vastly simplifies fermenter design including those employing algae, since there are no waste gases. Assuming $N_2$ is balanced, all of the gases entering a photosynthetic bacterial fermenter are recombined into cell mass. Mass transfer of the gaseous substrates into the liquid phase is not expected to be rate limiting at low gravity since the gas and liquid phases can be made to exist in a state similar to an emulsion.

In the practice of the present invention, the amount of nitrogen present as a nutrient may be limited, if desired, in order to limit the percent protein in the final product. For example, when using the process of the present invention to produce product useful for human food, it may be desirable to limit the amount of protein in the final product to about 10–15%, which increases the carbohydrate content to as high as about 80%.

The process of this invention utilizes carbon monoxide as the sole source of carbon, i.e., there is no need to add any yeast extract or other complex organic substrates. The carbonaceous materials, regardless of type, must first be converted to carbon monoxide and hydrogen. This distinguishes the present process from previously known techniques.

The foregoing is considered as illustrative only of the principles of the invention. Further, because numerous modifications and changes will readily occur to those skilled in the art, it is not desired to limit the invention to the exact construction and operation shown and described, and accordingly all suitable modifications and equivalents may be resorted to falling within the scope of the invention as redefined by the claims which follow.

What is claimed is:

1. A process for producing single-cell protein, comprising the steps of:
    (a) combusting organic materials in limited oxygen or air to produce gaseous nutrients consisting essentially of carbon monoxide, carbon dioxide, hydrogen, and nitrogen;
    (b) contacting said gaseous nutrients with photosynthetic bacteria selected from the group consisting of the Rhodospirillales order of phototrophic bacteria; wherein said bacteria is of a type which is capable of metabolizing carbon monoxide in light; and
    (c) exposing said bacteria to radiant energy in a manner such that said nutrients are assimilated by said bacteria into bacterial cell mass.

2. A process in accordance with claim 1, wherein said nutrients are contacted by said bacteria under anaerobic conditions.

3. A process in accordance with claim 1, wherein said organic materials comprise biomass waste.

4. A process in accordance with claim 1, wherein said radiant energy comprises solar energy.

5. A process in accordance with claim 4, wherein said nutrients are exposed to said bacteria in a reactor into which solar energy is permitted to enter.

6. A process in accordance with claim 1, wherein said organic materials are combusted in the presence of air.

7. A process in accordance with claim 1, wherein said photosynthetic bacteria is selected from the group consisting of *Rhodocyclus gelatinosus, Rhodoseudomonas palustris, Rhodospirillum molischianum,* and *Rhodopseudomonas capsulata*.

8. A process in accordance with claim 1, wherein said bacterial cell mass comprises about 65% protein.

9. A process in accordance with claim 1, wherein said bacteria are present in an aqueous medium.

10. A process for producing single-cell protein, comprising the steps of:
   (a) providing gaseous nutrients consisting essentially of carbon monoxide, carbon dioxide; and hydrogen, and nitrogen;
   (b) contacting said nutrients and nitrogen with photosynthetic bacteria selected from the group consisting of the Rhodospirillales order of phototrophic bacteria; wherein said bacteria is of a type which is capable of metabolizing carbon monoxide in light; and
   (c) exposing said bacteria to radiant energy in a manner such that said nutrients are assimilated by said bacteria into bacterial cell mass.

11. A process in accordance with claim 10, wherein said nutrients are exposed to said bacteria in a reactor into which solar energy is permitted to enter.

12. A process in accordance with claim 10, wherein said nutrients are contacted by said bacteria under anaerobic conditions.

13. A process in accordance with claim 11, wherein said bacteria are present in an aqueous medium, and wherein said medium is sprayed into said gaseous nutrients.

14. A process in accordance with claim 11, wherein said bacteria are present in an aqueous medium, and wherein said gaseous nutrients are bubbled through said medium.

15. A process in accordance with claim 10, wherein said photosynthetic bacteria is selected from the group consisting of the Rhodospirillales order of phototrophic bacteria.

16. A process in accordance with claim 10, wherein said bacterial cell mass comprises about 65% protein.

17. A process in accordance with claim 10, wherein said bacteria are present on a permeable support on the surface of a liquid medium, and wherein said bacteria are exposed to an atmosphere comprising said gaseous nutrients.

18. A process in accordance with claim 17, wherein said nitrogen is present in said aqueous medium.

19. A process in accordance with claim 18, wherein said nitrogen is present in a combined form as a compound selected from the group consisting of ammonia, urea, and a nitrate.

* * * * *